(12) United States Patent
Dar et al.

(10) Patent No.: US 7,149,582 B2
(45) Date of Patent: Dec. 12, 2006

(54) SCANNING ELECTRODE SYSTEM FOR A NEUROPROSTHESIS

(75) Inventors: Amit Dar, Hazabar (IL); Roger H. Nathan, Zamenhof (IL)

(73) Assignee: N.E.S.S. Neuromuscular Electrical Stimulation Systems Ltd., Ra'Anana (IL)

(*) Notice: Subject to any disclaimer, the term of this patent is extended or adjusted under 35 U.S.C. 154(b) by 498 days.

(21) Appl. No.: 10/321,637

(22) Filed: Dec. 18, 2002

(65) Prior Publication Data
US 2003/0114894 A1 Jun. 19, 2003

Related U.S. Application Data

(60) Provisional application No. 60/340,277, filed on Dec. 18, 2001.

(51) Int. Cl.
*A61N 1/04* (2006.01)

(52) U.S. Cl. .............. 607/48; 607/2; 607/49; 607/63; 607/68

(58) Field of Classification Search .............. 607/2, 607/48–49, 63–68
See application file for complete search history.

(56) References Cited

U.S. PATENT DOCUMENTS

| | | | | |
|---|---|---|---|---|
| 4,102,348 A | * | 7/1978 | Hihara et al. | 607/63 |
| 4,108,164 A | * | 8/1978 | Hall, Sr. | 600/594 |
| 4,177,819 A | * | 12/1979 | Kofsky et al. | 607/63 |
| 4,392,496 A | * | 7/1983 | Stanton | 607/48 |
| 4,580,569 A | * | 4/1986 | Petrofsky | 607/48 |
| 4,863,157 A | * | 9/1989 | Mendel et al. | 482/62 |
| 5,070,873 A | * | 12/1991 | Graupe et al. | 607/48 |
| 5,097,833 A | * | 3/1992 | Campos | 607/68 |
| 5,330,516 A | * | 7/1994 | Nathan | 607/48 |
| 5,391,200 A | * | 2/1995 | KenKnight et al. | 607/129 |
| 5,458,625 A | * | 10/1995 | Kendall | 607/46 |
| 5,540,735 A | * | 7/1996 | Wingrove | 607/46 |
| 5,643,332 A | * | 7/1997 | Stein | 607/49 |
| 5,843,142 A | * | 12/1998 | Sultan | 607/49 |
| 5,861,017 A | * | 1/1999 | Smith et al. | 607/59 |
| 6,064,912 A | * | 5/2000 | Kenney | 607/48 |
| 6,445,955 B1 | * | 9/2002 | Michelson et al. | 607/46 |
| 6,456,885 B1 | * | 9/2002 | Shiba et al. | 607/48 |

* cited by examiner

*Primary Examiner*—Robert E. Pezzuto
*Assistant Examiner*—Deborah Malamud
(74) *Attorney, Agent, or Firm*—Mark M. Friedman

(57) ABSTRACT

A system for adjusting a spatial distribution of an electrical stimulation field across a scanning electrode, by a system user, including: (a) a scanning electrode for performing functional electrical stimulation (FES) of at least one muscle of a limb, the electrode having first and second electrically conductive areas, separated by an electrically insulating region for insulating therebetween; (b) a distribution mechanism for dividing a current between the areas to produce the spatial distribution of the stimulation field across these areas, the distribution mechanism for operative connection to a muscle stimulator providing electrical stimulation to the system, and (c) a control mechanism for controlling the distribution mechanism, so as to effect a smooth and continuous adjustment of the spatial distribution of the field.

30 Claims, 2 Drawing Sheets

SCANNING ELECTRODE SYSTEM FOR A NEUROPROSTHESIS

This application draws priority from U.S. Provisional Patent Application Ser. No. 60/340,277, filed Dec. 18, 2001.

FIELD AND BACKGROUND OF THE INVENTION

The present invention relates to a neuroprosthetic device for activating the body with functional electrical stimulation (FES), and more particularly, to a surface neuroprosthetic device that enables the device user facile on-line adjustment and fine-tuning of the local current density over the surface of the scanning electrode, so as to achieve optimal muscle response.

Neuroprostheses and therapeutic FES devices, based on surface stimulation, typically interface with the body limb through an array of surface electrodes positioned over the limb surface. Electrical stimulation delivered to the underlying limb musculature and neurological structures through the surface electrode array causes activation of the muscles, and controlled movement of the limb. Such devices are used for restoring active function to paralyzed or plegic body limbs in patients suffering disease or trauma to the central nervous system, in neurological conditions such as stroke, spinal cord injury, head injury, cerebral palsy and multiple sclerosis. Surface neuroprostheses use controlled electrical currents through electrodes placed on the surface of the body, in order to elicit contraction of selected muscles or to input sensory stimulus. Neuroprostheses can activate paralyzed muscles of the limb in an independent fashion, or in coordination with voluntary activation of muscles under natural neurological control. These devices are in use today for functional activities such as walking, standing, gripping or releasing objects, and are used both as a therapeutic modality and for improvement or restoration of activities of daily living.

The aspiration to facilitate the positioning of stimulating electrodes of FES devices over the activation points of impaired limb has evoked, in the prior art, the design and manufacture of devices that substantially conform to the shape of particular body sites and limb. Accurate positioning of the electrodes enables optimal muscle activation to give correct movement of the limb with minimum discomfort and fatigue. Typical examples of devices for stimulating particular body sites are Liberson et al., Arch. Phys. Med., 1961, 42: 101–105 and U.S. Pat. No. 4,697,808 to Larson, et al., for activating the lower limb, and U.S. Pat. No. 5,330,516 to Nathan and U.S. Pat. No. 5,562,707 to Prochazka, for activating the wrist or forearm.

The contact area of the surface electrode is an important factor in the performance of a neuroprosthesis device. Large surface area electrodes tend to disperse the stimulation field over a large skin area, and the stimulation current density passing through the skin is relatively low, resulting in relative sensory comfort. In this case, however, the resolution of the electrode is correspondingly low, as a relatively large region of excitable tissue immediately underlying the electrode may be activated (see Sagi et al., 3-D Current Density Distributions Under Surface Stimulation Electrodes, Med. & Biol. Eng. & Comp., 33, pp. 403–408, 1995).

Earlier electrodes, such as set forth in U.S. Pat. No. 4,736,752 to Munck, et al., teach the control of the current density across the electrode through the use of conductive ink and adhesive patterns. The deficiencies of such electrodes are manifest from the description hereinbelow.

It should be emphasized that accurate electrode placement is very important for surface neuroprostheses. The patient is required to ensure, each time he wishes to set up the neuroprosthesis device, that all the electrodes are positioned accurately over the motor points of the muscles to be activated. Even slight deviations in the placement of the electrode may deleteriously effect the response of the limb. Alternatively or additionally, such deviations from the proper positioning may cause undesired movements, discomfort and unnecessary fatigue. This phenomenon is particularly pronounced at certain body limb sites that have a number of different excitable tissues disposed within a small region, within which a controlled current must be applied. These systems often have electrode placement problems, because the stimulating electrode is relatively large and consequently, does not enable precise activation by selectively focussing on a small target region of excitable tissue while avoiding excitation of unwanted tissue underlying the electrode This phenomenon, which may be termed "crowding" of excitable tissue, is particularly problematic at two limb sites: the dorsal surface of the forearm, and the dorsi-flexor surface of the lower leg. In these locations, small variations in electrode placement tend to generate large changes in hand and foot posture respectively.

U.S. Pat. No. 6,038,485 to Axelgaard discloses a transcutaneous medical electrode. The electrode has a highly conductive grid including a plurality of arrays of electrical conductors (conductive inkspots) for controlling current distribution of directed electrical pulses. Electrical connectors are provided for establishing electrical communication with the conductive grid for switching ON or OFF the electrical conductors in each array. The conductive grid is supported by a moderately conductive sheet, or film, and a conductive adhesive is provided for removably coupling the sheet or film and the conductive grid to the body of a user. The device is configured such that the conductive ink spots can be switched on and off so as to control the local current density across the electrode.

In addition, U.S. Pat. No. 6,038,485 teaches thickening of the support layer in areas that a reduced current density is needed, or thinning of the support layer in areas that require a higher current density. However, this adjustment procedure requires removal of the electrode and considerable technical knowledge and experience. Adjustments of this electrode would clearly be carried out "off-line", as the electrode is unsuitable for on-line adjustment of a neuroprosthesis. Moreover, the tuning of a device having such an electrode would be generally beyond the skill of the user, such that the ministrations of an expert in the field of FES would be required.

It would be highly desirable in neuroprostheses for the device to be adjustable, while the system is in use, so as to enable the use of direct feedback from the resulting limb posture and movements to guide the system user to adjust the system proprioceptively to achieve an optimal response.

In summary, there is no known neuroprosthetic device that enables the patient to tune the local current density delivered to the skin surface, while working with the device, and without the help of a clinician. There is, therefore, a recognized need for, and it would be highly advantageous to have, a neuroprosthetic device that enables the patient to tune the local current density delivered to the skin surface, with facility, and without the help of a clinician, so as to activate the muscles in an optimal manner.

SUMMARY OF THE INVENTION

The present invention is a surface neuroprosthetic device that enables facile adjustment and fine-tuning of the local current density over the surface of a transcutaneous scanning electrode, so as to achieve optimal muscle response.

The design of the present invention enables adjustment of the effective positioning of the device electrodes, even by the patient, while the device is stimulating, hence giving the patient direct, on-line feedback of the efficacy of the adjustment. This enables the patient to set up the device on his limb, and carry out the fine adjustment of the electrode position by observing his limb respond to the adjustment. Having achieved optimal response, the patient works with the device until the electrode may require readjusting.

Thus, according to the teachings of the present invention there is provided a scanning electrode system for a neuroprosthetic device, the system enabling facile adjustment and fine-tuning of a spatial distribution of a local electrical stimulation field across a scanning electrode, by a system user, the scanning electrode system including: (a) at least one scanning electrode for the neuroprosthetic device, the scanning electrode for performing functional electrical stimulation (FES) of at least one muscle of a limb of the user; (b) a distribution mechanism for distributing a current to the at least one scanning electrode so as to produce a biased electrical stimulation field across the at least one scanning electrode, the distribution mechanism for operative connection to a muscle stimulator providing electrical stimulation to the scanning electrode system, and (c) control means for adjustment of the biased electrical stimulation field by means of the distribution mechanism, the control means designed and configured so as to be accessable to and operable by the system user.

According to another aspect of the present invention there is provided a method of performing functional electrical stimulation (FES) using a scanning electrode system for a neuroprosthetic device, so as to enable facile adjustment and fine-tuning of a spatial distribution of a local electrical stimulation field across a scanning electrode, by a user, the method including the steps of: (a) providing a device including: (i) at least one scanning electrode for the neuroprosthetic device, the scanning electrode for performing functional electrical stimulation (FES) of at least one muscle of a limb of the user; (ii) a distribution mechanism for distributing current to the at least one scanning electrode, the distribution mechanism for operative connection to a muscle stimulator providing power to the scanning electrode system, and (iii) control means for adjustment of the biased electrical stimulation field by means of the distribution mechanism, the control means designed and configured so as to be accessable to and operable by the user, and (b) operating the control means to produce a biased electrical field across the at least one scanning electrode, so as to adjust a response of the muscle.

According to yet another aspect of the present invention there is provided a scanning electrode system for a neuroprosthetic device, the system enabling facile adjustment and fine-tuning of a spatial distribution of a local electrical stimulation field across a scanning electrode, by a system user, the scanning electrode system including: (a) at least one scanning electrode for the neuroprosthetic device, the scanning electrode for performing functional electrical stimulation (FES) of at least one muscle of a limb of the user; (b) a distribution mechanism for distributing current to the at least one scanning electrode so as to produce a biased electrical stimulation field across the at least one scanning electrode, the distribution mechanism for operative connection to a muscle stimulator providing electrical stimulation to the scanning electrode system, and (c) control means for adjustment of the biased electrical stimulation field by means of the distribution mechanism, wherein the distribution mechanism is designed and configured to bias the electrical field in a substantially monotonic fashion.

According to further features in the described preferred embodiments, the scanning electrode is a transcutaneous stimulation electrode for covering at least a portion of a skin surface of the limb.

According to still further features in the described preferred embodiments, the electrical stimulation field is biased in a substantially monotonic fashion.

According to still further features in the described preferred embodiments, the at least one scanning electrode has two adjacent conductive regions, each of the regions being electrically connected with the distribution means, the regions being electrically isolated from one another.

According to still further features in the described preferred embodiments, the distribution mechanism includes a potentiometer.

According to still further features in the described preferred embodiments, the control means are designed and configured for facile adjustment of the biased electrical field by a typical user.

According to still further features in the described preferred embodiments, the control means are intuitive control means.

According to still further features in the described preferred embodiments, the intuitive control means are proprioceptive control means.

According to still further features in the described preferred embodiments, the control means are designed and configured such that a movement of the control means in a first direction effects a limb movement correction of the limb in the same direction.

According to still further features in the described preferred embodiments, the distribution mechanism and the control means are designed and configured such that the adjustment of the biased electrical stimulation field is effected simultaneously with the functional electrical stimulation of the muscle.

According to still further features in the described preferred embodiments, the scanning electrode system further includes: (d) a voice command unit for operating the control means.

According to still further features in the described preferred embodiments, the control means is operated by electromyograph-triggered commands.

According to still further features in the described preferred embodiments, the control means are designed and configured such that the adjustment of the biased electrical stimulation field is effected in a continuous fashion.

According to still further features in the described preferred embodiments, the scanning electrode system further includes: (d) an electrogoniometer, disposed on the limb, the control means being responsive to input from the electrogoniometer.

According to still further features in the described preferred embodiments, the operating of the control means responsive to input from the electrogoniometer is performed by the user.

According to still further features in the described preferred embodiments, the control means are designed and configured such that the adjustment of the biased electrical field is effected in a continuous fashion.

According to still further features in the described preferred embodiments, the operating of the control means to produce a biased electrical field across the at least one scanning electrode is performed so as to achieve an optimal muscle response.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
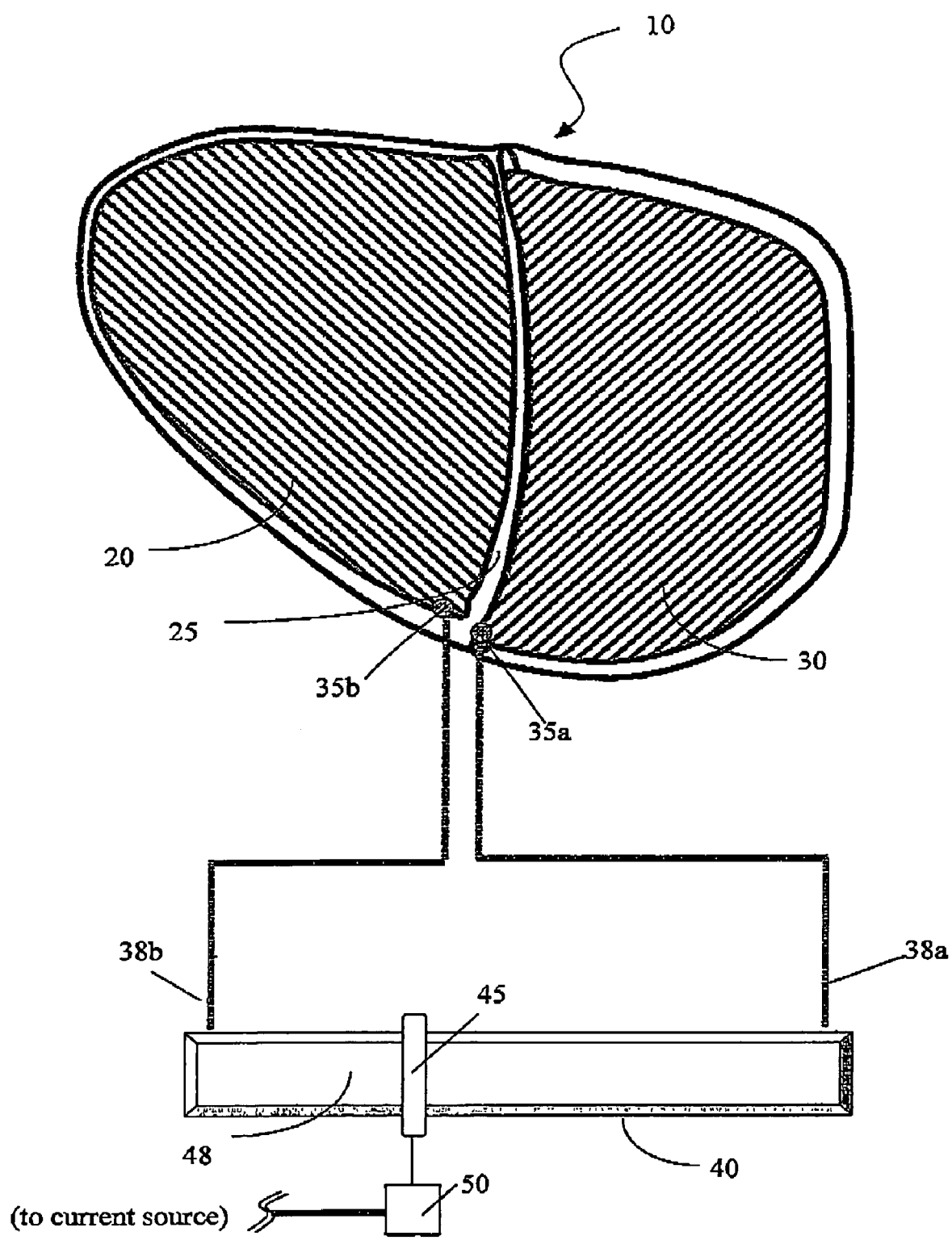
FIG. 1 is a schematic diagram of a transcutaneous surface scanning electrode device, according to the present invention.

The present invention is a surface neuroprosthetic device that enables facile adjustment and fine-tuning of the local current density over the surface of a transcutaneous scanning electrode, so as to achieve optimal muscle response.

The transcutaneous surface electrode of the present invention allows for adjustment of the local current density, by the user, while the device is stimulating, hence giving the user direct feedback of the efficacy of the adjustment. This enables the user to set up the device on his limb, and carry out the fine adjustment of the electrode position by observing and feeling the limb response to the adjustment. Having achieved optimal response, the patient works with the device until he finishes his exercise, or until the electrode requires an additional readjustment.

The principles and operation of the system and method according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The basis for the present invention is best understood against the background of the known art. One main drawback of the art taught by the above-referenced patent to Axelgaard is that the control of the local current density is achieved by switching in and out a plurality of conductive inkspots ranged as a two-dimensional grid. This requires very high level of expert knowledge on the part of the patient to understand the correspondence between switching in or out of an inkspot and the resulting change in limb posture and movement. Having made a change to the stimulation field distribution over the electrode surface, the patient has no methodically logical means to know how to proceed further with the adjustment.

Referring now to the drawings, FIG. 1 is a schematic diagram of a transcutaneous surface scanning electrode device for FES of impaired limbs, according to the present invention.

A scanning electrode 10, which conforms to the site for which it is intended, preferably has the approximate shape of the skin region over the intended stimulation site. Scanning electrode 10 includes conductive area 20 and conductive area 30, separated by insulating area 25. Insulating area 25 may simply be a gap between conductive areas 20 and 30, or alternatively, insulating area 25 may consist of a material having a significantly reduced electrical conductivity with respect to the materials used in conductive areas 20 and 30.

A potentiometer 40, powered by stimulation current source 50, is electrically connected to conductive areas 20 and 30. A first end of potentiometer 40 is connected via electrical wire 38a and via conductive connectors 35a to conductive area 30. A second end of potentiometer 40 is connected via electrical wire 38b and via conductive connectors 35b to conductive area 20. Conductive connectors 35a and 35b are disposed on conductive areas 30 and 20, respectively. Potentiometer 40 is connected to a muscle stimulator 50.

Potentiometer 40 is used to produce a substantially continuous electrical field across scanning electrode 10, the field having a gradient between conductive area 20 and conductive area 30. The bias of the electrical field is adjusted by means of moving lever 45 of potentiometer 40, as will be explained in further detail hereinbelow.

Scanning electrode 10 is intended to be positioned within the neuroprosthesis such that when placed on to the body limb, scanning electrode 10 overlies the body of a single target muscle, of multiple target muscles, or muscle/nerve complex such that adjustment of the electrode field bias by moving lever 45 of potentiometer 40 in one direction tends to direct the limb posture or limb movement correction to the same direction—allowing proprioceptive and hence "obvious" or "natural" control of the limb. The simplicity afforded by the present invention, of lever 45-controlled movement corresponding to limb movement adjustment, allows a patient to carry out a time-consuming and difficult adjustment of the electrode placement, in a very fast and simple manner. Consequently, the patient can effectively use the neuroprosthesis at home on a daily basis, without clinical supervision.

It must be emphasized that in contrast to a regular stimulation electrode, which generates a spatially fixed electrical field in the underlying body tissue, the scanning electrode utilized in the present invention enables the user-guided movement of the electrical field through the tissue.

It must be further emphasized that while the scanning electrode described hereinabove is a transcutaneous stimulation electrode, other electrode types fall within the broad scope of the invention, including various implanted scanning electrodes, e.g., scanning electrodes for direct stimulation of nerves disposed on adjacent nerve branches, scanning micro-electrodes for direct stimulation of nerve fascicles, scanning epimysial electrodes contacting the muscle epimysium, and scanning electrodes for intramuscular implantation.

Other possible ways for the system user to adjust the scanning electrode may depend on availability of residual voluntary movements that can be utilized by the user to slide potentiometer lever 45. Voice commands and EMG (electromyograph)-triggered input command systems are well-known technologies that could be applied to control the distribution of the stimulation between the two sections of the scanning electrode. Instead of potentiometer 40, other electronic means could be used to control the distribution of the stimulation current between the two sides of the scanning electrode.

The sliding of lever 45 of potentiometer 40 to one extreme position of slider 48 elicits one extreme of motion or of posture; moving lever 45 to the other extreme of slider 48 elicits the other motion or posture extreme. A full-range value of typically 500Ω, is suitable for the resistor of potentiometer 40. The patient can also slide lever 45 to any position between these two extremes of slider 48 in order to elicit an intermediate motion or posture, as desired.

As used herein in the Specification and in the claims section that follows, the term "typical user" refers to a user having routine knowledge and experience with neuroprosthetic devices. The term "typical user" is meant to specifically exclude doctors, clinicians, etc., having expertise in the field of neuroprostheses.

As used herein in the Specification and in the claims section that follows, the term "monotonic" is used in the mathematical sense to refer to a sequence or set of points, the successive members of which either consistently increase or decrease, but do not oscillate in relative value. In a preferred embodiment of the scanning electrode of the instant invention, the stimulation current is distributed across regions of at least one scanning electrode to produce a monotonically increasing or decreasing stimulation field.

Even if moving lever 45 is oriented in a direction that is not proprioceptive, e.g., in a forward-backward orientation instead of the above-described left-right orientation, there are several inventive distinctions with respect to the prior art. Moving lever 45, which could be a knob or another type of activator known in the art, provides the user with an intuitive means of controlling the limb, similar to moving a knob or lever for proprioceptive centering of the stereophonic output between two speakers using audio feedback. The desired position lies upon a continuum. The user can perform a tuning operation, moving the knob or lever back and forth until the optimal position is attained, for example, rotating his foot to the left and to the right until the foot points straight forward. It is intuitively obvious to the user to reverse the direction of the knob or lever once the optimal point has been passed, such that the user can move towards the optimal point with confidence and certainty, and in the event that the point has been passed, the user can also return towards the optimal point with confidence and certainty.

Moreover, in sharp contrast to the device disclosed by U.S. Pat. No. 6,038,485, the adjustment is continuous, and is designed to be effected while the device is stimulating. The user can see the change in movement or posture visually, while carrying out the proprioceptive adjustment of lever 45. This arrangement allows simple, fast fine-tuning of the effective position of electrode 10 while the neuroprosthesis is in use.

It follows from all of the above that the donning and adjusting of a neuroprosthesis device with a scanning electrode of the present invention can be done by the user whenever he wishes, without the help of a clinician or other trained personnel.

In another preferred embodiment, automatic self-tuning of the neuroprosthesis is enabled by utilizing a sensor such as an electrogoniometer, force sensors or electromyographic monitoring to sense the movement or posture of the limb, and to provide feedback information thereon. The potentiometer could be adjusted in closed loop to optimize or balance the biomechanical output.

Figure 2:
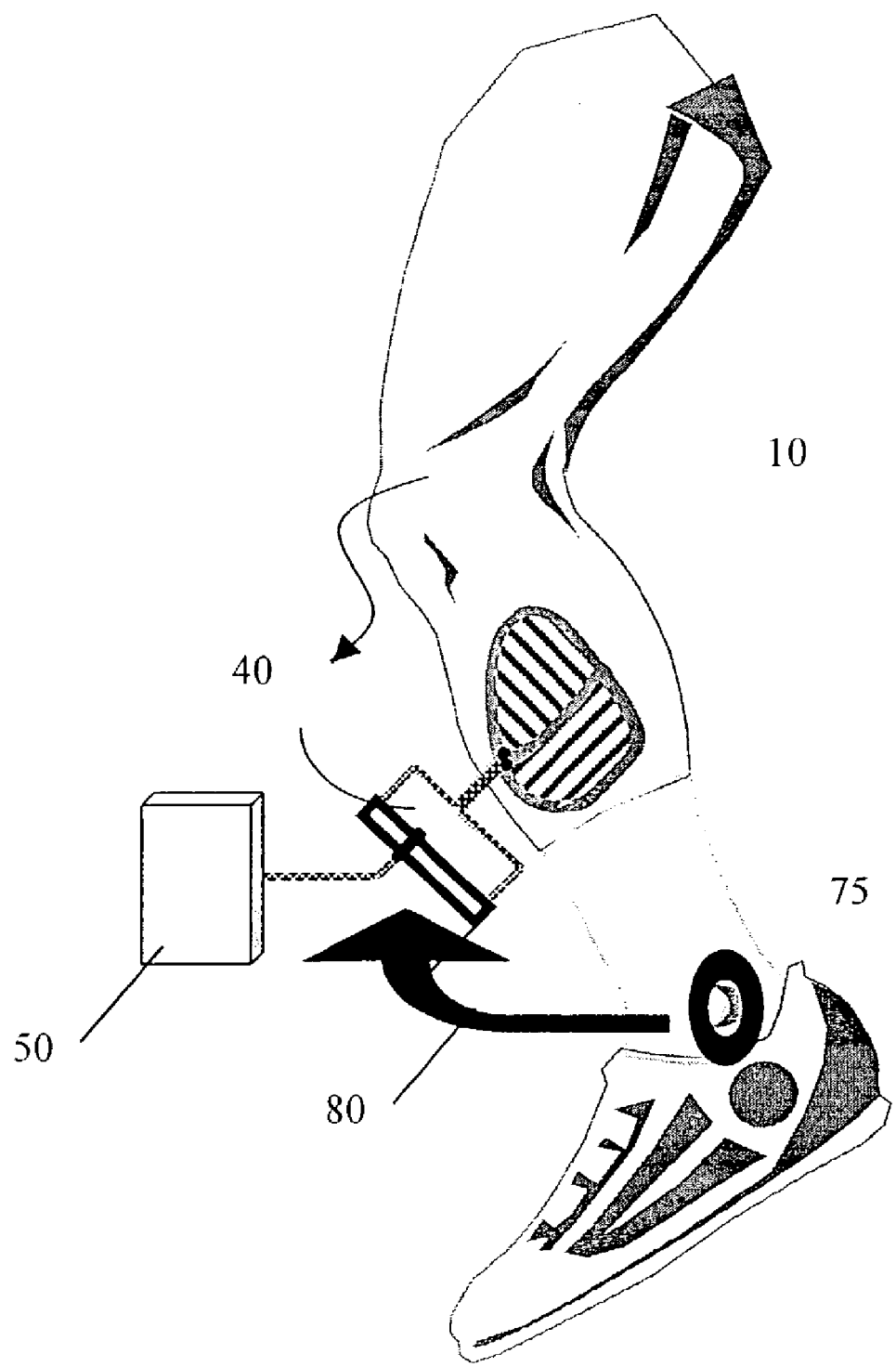
FIG. 2 is a schematic diagram depicting the monitoring of an ankle joint angle by an electrogoniometer, and the resultant feedback control on the potentiometer settings.

The monitoring of an ankle joint angle by an electrogoniometer 75 is illustrated schematically in FIG. 2. The correction required to reach the target ankle joint angle is used in a feedback loop 80 to adjust/control potentiometer 40, which carries out the desired correction to the distribution of the stimulation current over scanning electrode 10, and the muscle activation is modulated to achieve this correction. As in FIG. 1, potentiometer 40 is connected to a muscle stimulator 50.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A scanning electrode system for a neuroprosthetic device, the system for providing facile adjustment and fine-tuning of a spatial distribution of a local electrical stimulation field across a scanning electrode, by a system user, the scanning electrode system comprising:

(a) at least one scanning electrode for the neuroprosthetic device, said scanning electrode for performing functional electrical stimulation of at least one muscle of a limb of the user, wherein within a single electrode of said at least one scanning electrode there is disposed at least a first electrically conductive area and a second electrically conductive area, said electrically conductive areas separated by an electrically insulating region for insulating therebetween;

(b) a distribution mechanism for dividing a current between said electrically conductive areas so as to produce the spatial distribution of the electrical stimulation field across said electrically conductive areas, said distribution mechanism for operative connection to a muscle stimulator providing electrical stimulation to the scanning electrode system, and (c) a control mechanism for controlling said distribution mechanism, so as to effect a smooth and continuous adjustment of the spatial distribution of the electrical stimulation field.

2. The scanning electrode system of claim 1, wherein said scanning electrode is a transcutaneous stimulation electrode.

3. The scanning electrode system of claim 1, wherein the scanning electrode system is designed and configured such that the spatial distribution of the electrical stimulation field is substantially monotonic.

4. The scanning electrode system of claim 1, wherein said distribution mechanism includes a potentiometer.

5. The scanning electrode system of claim 1, wherein said control mechanism is designed and configured for adjustment of the electrical stimulation field by a typical user.

6. The scanning electrode system of claim 1, wherein said distribution mechanism includes a potentiometer, said potentiometer for adjusting the spatial distribution of the electrical stimulation field.

7. The scanning electrode system of claim 1, wherein said control mechanism is a proprioceptive control mechanism, such that a movement of said control mechanism in a first direction effects a limb movement correction of said limb in said direction.

8. The scanning electrode system of claim 6, wherein said control mechanism is designed and configured such that a continuous movement of said control mechanism in a first direction effects a continuous limb movement correction of said limb in said direction.

9. The scanning electrode system of claim 1, wherein said distribution mechanism and said control mechanism are designed and configured such that said adjustment of the spatial distribution of the stimulation field is effected simultaneously with said functional electrical stimulation of said muscle.

10. The scanning electrode system of claim 1, further comprising:
   (d) a voice command unit for operating said control mechanism.

11. The scanning electrode system of claim 1, wherein said control mechanism is operated by electromyograph-triggered commands.

12. The scanning electrode system of claim 1, further comprising:
   (d) an electrogoniometer, disposed on said limb, said control mechanism being responsive to input from said electrogoniometer.

13. The scanning electrode system of claim 1, wherein said control mechanism includes a sliding mechanism for effecting said smooth and continuous adjustment.

14. A method of performing functional electrical stimulation (FES) using a scanning electrode system for a neuroprosthetic device, so as to enable facile adjustment and fine-tuning of a spatial distribution of a local electrical stimulation field across a scanning electrode, by a user, the method comprising the steps of:
   (a) providing a device including:
      (i) at least one scanning electrode for the neuroprosthetic device, said scanning electrode for performing functional electrical stimulation of at least one muscle of a limb of the user, wherein within a single electrode of said at least one scanning electrode there is disposed at least a first electrically conductive area and a second electrically conductive area, said electrically conductive areas separated by an electrically insulating region for insulating therebetween;
      (ii) a distribution mechanism for dividing a current between said electrically conductive areas so as to produce the spatial distribution of the electrical stimulation field across said electrically conductive areas, said distribution mechanism for operative connection to a muscle stimulator providing electrical stimulation to the scanning electrode system, and
   (b) controlling said distribution mechanism to effect a smooth and continuous adjustment of the spatial distribution of the electrical stimulation field, so as to adjust a response of said muscle.

15. The method of claim 14, wherein said controlling of said distribution mechanism is performed by a typical user.

16. The method of claim 14, wherein said distribution mechanism includes a potentiometer.

17. The method of claim 14, wherein said controlling is performed by means of a proprioceptive control mechanism, such that a movement of said control mechanism in a first direction effects a limb movement correction of said limb in said direction.

18. The method of claim 14, wherein said controlling is performed by means of a control mechanism, and wherein said operating of said control mechanism is effected simultaneously with said functional electrical stimulation of said muscle of the user.

19. The method of claim 14, wherein said controlling includes using a voice control.

20. The method of claim 14, wherein said controlling includes using an electromyographic control.

21. The method of claim 14, wherein said scanning electrode is a transcutaneous stimulation electrode for covering at least a portion of a skin surface of said limb.

22. The method of claim 14, wherein said controlling is performed so as to achieve an optimal muscle response of said muscle.

23. A scanning electrode system for a neuroprosthetic device, the system for providing facile adjustment and fine-tuning of a spatial distribution of a local electrical stimulation field across a scanning electrode, by a system user, the scanning electrode system comprising:
   (a) at least one scanning electrode for the neuroprosthetic device, said scanning electrode for performing functional electrical stimulation (FES) of at least one muscle of a limb of the user, said scanning electrode having at least a first electrically conductive area and a second electrically conductive area, said electrically conductive areas separated by an electrically insulating region for insulating therebetween, said electrically conductive areas having a substantially identical polarity;
   (b) a distribution mechanism for dividing a current between said electrically conductive areas so as to produce the spatial distribution of the electrical stimulation field across said electrically conductive areas, said distribution mechanism for operative connection to a muscle stimulator providing electrical stimulation to the scanning electrode system, and
   (c) a control mechanism for controlling said distribution mechanism, so as to effect a smooth and continuous adjustment of the spatial distribution of the electrical stimulation field.

24. The scanning electrode system of claim 23, wherein the scanning electrode system is designed and configured such that the spatial distribution of the electrical stimulation field is substantially monotonic.

25. The scanning electrode system of claim 23, wherein said distribution mechanism includes a potentiometer.

26. The scanning electrode system of claim 23, wherein said control mechanism is designed and configured for adjustment of the electrical stimulation field by a typical user.

27. The scanning electrode system of claim 23, wherein said distribution mechanism includes a potentiometer, said potentiometer for adjusting the spatial distribution of the electrical stimulation field.

28. The scanning electrode system of claim 23, wherein said control mechanism is a proprioceptive control mechanism, such that a movement of said control mechanism in a first direction effects a limb movement correction of said limb in said direction.

29. The scanning electrode system of claim 27, wherein said control mechanism is designed and configured such that a continuous movement of said control mechanism in a first direction effects a continuous limb movement correction of said limb in said direction.

30. The scanning electrode system of claim 23, wherein said control mechanism is a proprioceptive control mechanism, such that a movement of said control mechanism in a first direction effects a limb movement correction of said limb in said first direction, and wherein a movement of said control mechanism in a second direction effects a limb movement correction of said limb in said second direction.

* * * * *